United States Patent [19]

Edwards

[11] 3,982,010

[45] Sept. 21, 1976

[54] THIAZOLE CARDIOVASCULAR AGENTS

[75] Inventor: John A. Edwards, Los Altos, Calif.

[73] Assignee: Syntex (U.S.A.) Inc., Palo Alto, Calif.

[22] Filed: Sept. 19, 1974

[21] Appl. No.: 507,651

Related U.S. Application Data

[60] Division of Ser. No. 289,730, Sept. 15, 1972, Pat. No. 3,850,945, which is a continuation-in-part of Ser. No. 193,172, Oct. 27, 1971, abandoned.

[52] U.S. Cl. .............................. 424/270; 424/248; 424/267
[51] Int. Cl.$^2$ ..................................... A61K 31/425
[58] Field of Search ............ 424/270, 248, 274, 267

[56] References Cited
UNITED STATES PATENTS

| | | | |
|---|---|---|---|
| 3,328,417 | 6/1967 | McLoughlin et al. | 260/302 R |
| 3,631,055 | 12/1971 | Posselt et al. | 260/302 R |
| 3,729,469 | 4/1973 | Wasson | 260/293.68 |
| 3,850,945 | 11/1974 | Edwards | 260/302 R |

*Primary Examiner*—Leonard Schenkman
*Attorney, Agent, or Firm*—Lawrence S. Squires; William B. Walker

[57] ABSTRACT

1-Amino-3-[2-thiazoloxy]-2-propanol and substituted 1-amino derivatives thereof; 3-[2-thiazoloxy]-1,2-epoxypropane 5-[thiazol-2-oxymethylene]-oxazolidine and/or N-substituted and/or 2-substituted oxazolidine, derivatives thereof and methods of preparing such compounds. The above 1-amino-3-[2-thiazoloxy]-2-propanol and derivatives exhibit β-adrenergic stimulating cardiovascular activity and are useful for the treatment of abnormal heart conditions in mammals. The above 3-[2-thiazoloxy]-1,2-epoxypropane and derivatives are useful as intermediates for the aforementioned cardiovascular agents. The 5-[thiazol-2-oxymethylene]-oxazolidine and derivatives are intermediates for aforementioned cardiovascular agents. The 1-amino-3-[2-thiazoloxy]-2-propanol and derivatives can be prepared by base or acid hydrolysis of the corresponding 5-[thiazol-2-oxymethylene]-oxazolidine or derivatives; or by treatment of the corresponding 3-[2-thiazoloxy]-2,3-epoxypropane or derivative with the desired amine or amino-derivative.

7 Claims, No Drawings

THIAZOLE CARDIOVASCULAR AGENTS

This application is a division of U.S. Ser. No. 289,730, filed Sept. 15, 1972, now U.S. Pat. No. 3,850,945 which in turn is a continuation-in-part of U.S. Ser. No. 193,172, filed Oct. 27, 1971 and now abandoned.

BACKGROUND OF THE INVENTION

1. Field of the Invention

This invention relates to pharmaceutical compositions comprising the 1-amino-3-(thiazol-2-oxy)-2-propanol and derivatives, of the invention, and to methods of applying such compositions for the treatment of mammals.

2. The Prior Art

At the present time the compound generally relied on for the treatment of heart failure and especially acute heart failure is 3,4-dihydroxy-α-[(isopropylamino)methyl]-benzyl alcohol (note U.S. Pat. Nos. 2,308,237 and 2,715,141). This compound produces a marked increase in heart rate and contractile force but regrettably is short acting and decreases blood pressure. Further, this compound has, as an undesirable side effect, a propensity to induce arrhythmia. Accordingly the present invention relates to the discovery of compounds which are useful in the treatment of abnormal cardiovascular conditions, including heart failure, and which are long acting and exhibit only minimal effects on blood pressure and possess a very low arrhythmogenic potential.

SUMMARY

In summary the compounds of the invention can be represented by the following generic formula:

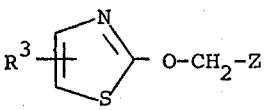

wherein $R^3$ is hydrogen; at either the 4- or 5-position selected from the group Z is selected from the group having the formulas:

—CHOH—CH$_2$—Z';

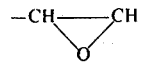

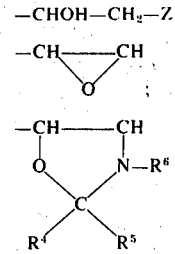

wherein Z' is amino or amino derivative or nitrogen heterocycle; $R^6$ is hydrogen, lower alkyl, aryl or arylalkyl; $R^4$ and $R^5$ are independently selected from the group of hydrogen, lower alkyl, arylalkyl or together with the carbon atom to which they are joined form a cycloalkyl having from 5 through 7 carbon atoms.

Also encompassed within the invention are pharmaceutically acceptable salts of the above compounds.

In summary the process of the invention of preparing the compounds, of the invention, wherein Z is

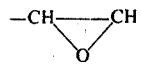

comprises epoxidizing the corresponding 3-(thiazol-2-oxy)-1-alkylsulfonyl or phenylsulfonyl-2-propanol derivative at the 2,3-position, typically via treatment with a strong base.

In summary the process of the invention for preparing the compounds, of the invention, wherein Z is the group —CHOH—CH$_2$—Z' comprises treating the compounds of the invention wherein Z is

—CH———CH
    \\O/ with ammonia or amine having the desired $R^1$ and/or $R^2$ substituent. Alternatively these compounds can be prepared, according to the invention, by hydrolysis of the corresponding Z is oxazolidine compounds of the invention.

In summary the process of the invention of preparing the compounds of the invention wherein Z is an -oxazolidine group comprises condensation of a 2-bromo or -chloro-thiazole having the desired $R^3$ (i.e., 4- or 5-position) substituent with a 5-hydroxymethyl-oxazolidine having the desired $N_3$-substituent. Alternatively the oxazolidine compounds can be prepared by treatment of the corresponding compounds of the invention where Z is a propanol derivative.

In summary the pharmaceutical compositions of the invention include both solutions and solids or powders comprising one or more of the compounds, of the invention, wherein Z is a propanol derivative and/or one or more compounds, of the invention, wherein Z is an oxazolidine derivative in combination with a suitable pharmaceutical solution (e.g., sterile water) or pharmaceutical solid excipients.

The invention will be further described herein below.

FURTHER DESCRIPTION OF THE INVENTION AND PREFERRED EMBODIMENTS

The compounds of the invention can be represented by the following sub-generic formulas:

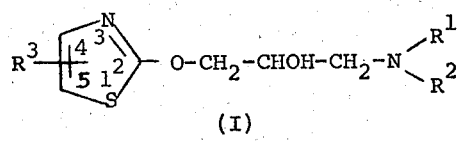

(I)

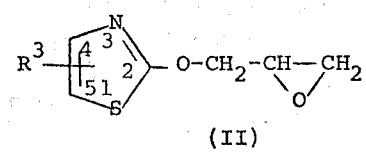

(II)

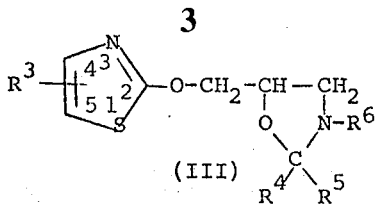

(III)

wherein R¹ and R² are independently selected from the group of hydrogen, lower alkyl, cycloalkyl having from 3 through 7 ring atoms, lower alkenyl, aryl, arylalkyl, lower alkylaryl, hydroxy lower alkyl, (lower alkoxy) lower alkyl, lower alkyl(N-heterocyclic having from 5 through 7 ring atoms including one or two heteroatoms selected from the group of nitrogen, oxygen and sulfur and wherein at least one of said heteroatoms is nitrogen) and the group

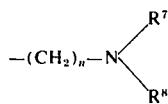

wherein $R^7$ and $R^8$ are independently hydrogen or lower alkyl, and n is a whole integer of from 1 through 4, or R¹ and R² together with the nitrogen atom to which they are joined form a nitrogen heterocycle having from 5 through 7 ring atoms having 1 or 2 hetero atoms selected from the group consisting of nitrogen, oxygen and sulfur and wherein at least one of said hetero atoms is nitrogen or R¹ and R² form a substituted nitrogen heterocycle having from 5 through 7 ring atoms including one or two heteroatoms selected from the group of nitrogen, oxygen and sulfur and wherein at least one of said heteroatoms is nitrogen and having one or two substituents independently selected from the group of lower alkyl, and hydroxy(lower alkyl);

R³ is hydrogen;

R⁶ is hydrogen, lower alkyl, aryl or arylalkyl.

Also encompassed within the invention are pharmaceutically acceptable salts of the above compound of formulas I and III.

The compounds of the invention have an asymmetric carbon atom in the propane side chain and thus exist as optical isomers. Correspondingly the above formulas are intended to represent the respective individual (+) and (−) optical isomers as well as mixtures of such isomers and the individual isomers as well as mixtures thereof are encompassed within the invention. Where the compounds of the invention have 1-positioned substituents, on the propane chain, which have asymmetric atoms, the compounds exhibit further optical activity with respect to such asymmetric atoms. Correspondingly, formulas I and III are intended to represent the individual respective optical isomers as well as mixtures of such isomers and the individual isomers as well as mixtures thereof are encompassed within the invention.

The term lower alkyl refers to both straight and branched chain alkyl groups having a total of from 1 through 6 carbon atoms and thus includes primary, secondary and tertiary alkyl groups. Typical lower alkyls include, for example, methyl, ethyl, n-propyl, isopropyl, n-butyl, t-butyl, n-hexyl and the like. The term cycloalkyl refers to cyclic hydrocarbon groups having from 3 through 7 carbon atoms such as, for example, cyclopropyl, cyclopentyl, cycloheptyl, and the like. The term lower alkenyl refers to monoethylenically unsaturated aliphatic groups having from 2 through 6 carbon atoms and wherein the double bond can be between any two adjacent carbon atoms. Typical lower alkenyl groups include, for example, vinyl, propenyl, and the like. The term lower alkoxy refers to the group having the formula R'O— wherein R' is lower alkyl. Typical alkoxy groups include, for example, methoxy, ethoxy, t-butoxy and the like. The term (lower alkoxy) lower alkyl refers to the group —R'—OR' wherein R' is lower alkyl and OR' is lower alkoxy. The term hydroxy lower alkyl refers to groups having the formula HOR'— wherein R' is lower alkyl. Typical hydroxy-alkyl groups include, for example, hydroxymethyl, α-hydroxy-ethyl, β-hydroxypropyl, hydroxyisopropyl, hydroxy-t-butyl and the like. The term carboxy refers to the group —COOH. The term "halo" refers to iodo, bromo, chloro and fluoro groups. The term "acyl" refers to acyl groups derived from carboxylic acids having from 1 through 12 carbon atoms such as acetyl, propionyl, butyryl, valeryl, isovaleryl, hexanoyl, heptanoyl, octanoyl, nonanoyl, undecanoyl, lauroyl, benzoyl, phenylacetyl, phenylpropionyl, o-, m-, p-toluoyl, β-cyclopentylpropionyl, formyl and the like.

The term "alkoxycarbonyl" refers to groups having the formula

wherein $R_3'$ is an alkyl group having from 1 through 11 carbon atoms. Typical alkoxycarbonyl groups thus include, for example, methoxycarbonyl, propoxycarbonyl, isopropoxycarbonyl, undecanoxycarbonyl, and the like. The term acyloxy refers to groups derived from carboxylic acids having from 2 through 12 carbon atoms such as acetyloxy, propionyloxy, butyryloxy, valeryloxy, isovaleryloxy, hexanoyloxy, heptanoyloxy, octanoyloxy, nonanoyloxy, undecanoyloxy, lauroyloxy, benzoyloxy, phenylacetyloxy, phenylpropionyloxy, o-, m-, p-toluoyloxy, β-cyclopentylpropionyloxy, and the like.

By the term "aryl" is meant a group containing one aromatic ring having up to 10 carbons and preferably is phenyl. By the term "alkylaryl" is meant a substituted phenyl group having one or more alkyl substituents and having up to 10 carbon atoms such as o-tolyl, m-tolyl, p-isopropylphenyl, 2,3-dimethylphenyl, 3,5-dimethylphenyl, and the like. By the term "arylalkyl" is meant a phenyl (or substituted phenyl) substituted alkyl group such as benzyl, phenylethyl, β-(p-hydroxyphenyl)ethyl, and the like preferably having up to 12 carbons. The term "substituted phenyl" refers to phenyl groups substituted at one or more of the ortho, meta or para positions with a hydroxy, lower alkyl, acyloxy, lower alkoxy or halo groups. Typical substituted phenyl groups include, for example, p-hydroxyphenyl, p-tolyl, p-acetoxyphenyl, p-nitrophenyl, p-fluorophenyl, p-chlorophenyl and the corresponding ortho and meta isomers.

The term lower alkylamino refers to the group having the formula R'HN— wherein R' is lower alkyl. The term dialkylamino refers to the group having the formula $R_1'R_2'N$ wherein $R_1'$ and $R_2'$ are independently lower alkyl. Typical dialkylamino groups include, for example, dimethylamino, N-methyl-N-ethylamino, diethylamino, N-t-butyl-N-isopropylamino, and the like.

The term N-heterocycle or nitrogenheterocycle refer to both saturated and unsaturated heterocyclics having from 5 through 7 ring atoms, one of which is nitrogen and which can optionally also contain a second heterocycle ring atom selected from the group of nitrogen, sulfur and oxygen. Also encompassed within the term are substituted N-heterocyclics having one or two substituents independently selected from the group of lower alkyl, hydroxylower alkyl, and halo. Typical N-heterocycles are, for example, shown by way of formula illustration on page 12 of the ultimate parent application, U.S. Ser. No. 193,172 filed Oct. 27, 1971, hereby incorporated by reference.

The term N-heterocycle alkyl refers to a lower alkyl group having a N-heterocyclic substituent as defined herein above. Such groups can be represented by the formula XR′ — wherein X is N-heterocyclic and R′ is lower alkyl.

The term pharmaceutically acceptable salts refers to pharmaceutically acceptable hydrogen-anion addition salts and pharmaceutically acceptable salts of the $R^3$-carboxy group or the $R^3$-sulfonyl group, inclusively, which do not adversely affect the pharmaceutical properties of the parent compounds. With respect to the addition salts, suitable inorganic anions include, for example, chloride, bromide, iodide, sulfate, phosphate, carbonate, nitrate, hydrocarbonate, sulfite, sulfate and the like. Suitable organic anions include, for example, acetate, benzoate, lactate, picrate, propionate, butyrate, valerate, tartrate, maleate, fumarate, citrate, succinate, tosylate, ascorbate, pamoate, nicotinate, adipate, glyconate, and the like. With respect to the salts of the $R^3$-carboxy and $R^3$-sulfonyl groups (i.e. carbonate and sulfate salts) suitable cations include, for example, sodium, potassium, aluminum, calcium, iron, magnesium, and the like.

Typical illustrations of the compounds of formula I can be had, for example herein below, by reference to Examples 4–10. The preferred $R^1$ and $R^2$ substituents are those wherein one of $R^1$ or $R^2$ is hydrogen and the other is selected from the group of isopropyl; secbutyl; cyclopropyl; cyclopentyl; α-phenylethyl; γ-phenylpropyl; β-(3,4-dimethoxyphenyl)-ethyl; β-(p-hydroxyphenyl)-ethyl; α-methyl-β-(p-hydroxyphenyl)-ethyl; γ-(p-hydroxyphenyl)-propyl; and α-methyl-γ-(p-hydroxyphenyl)-propyl; and especially isopropyl. The particularly preferred compounds of formula I wherein $R^3$ is hydrogen are:

1-isopropylamino-3-(thiazol-2-oxy)-2-propanol;
1-[β-(3,4-dimethoxyphenyl)-ethylamino]-3-(thiazol-2-oxy)-2-propanol;
1-sec-butylamino-3-(thiazol-2-oxy)-2-propanol;
1-cyclopropylamino-3-(thiazol-2-oxy)-2-propanol;
1-cyclopentylamino-3-(thiazol-2-oxy)-2-propanol;
(+)-1-α-phenylethylamino-3-(thiazol-2-oxy)-2-propanol;
1-γ-phenylpropylamino-3-(thiazol-2-oxy)-2-propanol;
1-[γ-(p-hydroxyphenyl)-ethylamino]-3-(thiazol-2-oxy)-2-propanol;
1-[α-methyl-β-(p-hydroxyphenyl)-ethylamino]-3-thiazol-2-oxy)-2-propanol;
1-[γ-(p-hydroxyphenyl)-propylamino]-3-(thiazol-2-oxy)-2-propanol; and
1-[α-methyl-γ-(p-hydroxyphenyl)-propylamino]-3-(thiazol-2-oxy)-2-propanol.

Typical illustrations of the compounds of formula II can be had, for example, herein below, by reference to Example 3.

Typical illustrations of the compounds of formula III can be had, herein below, by reference to Examples 12, 13 and 17. The preferred $R^4$- and $R^5$-substituents are those wherein $R^4$ and $R^5$ are each hydrogen or are each methyl. The preferred $R^6$ groups are isopropyl, sec-butyl, cyclopropyl, cyclopentyl, α-phenylethyl, γ-phenylpropyl, β-(3,4-dimethoxyphenyl)-ethyl, β-(p-hydroxyphenyl)-ethyl, α-methyl-β-(p-hydroxyphenyl)-ethyl, γ-(p-hydroxyphenyl)-propyl and α-methyl-γ-(p-hydroxyphenyl)-propyl and especially isopropyl.

The particularly preferred compounds of formula III wherein $R^3$ is hydrogen are:

thiazol-2′-oxy-5-methylene-N-isopropyloxazolidine;
thiazol-2′-oxy-5-methylene-N-[β-(3,4-dimethoxyphenyl)ethyl]-oxazolidine;
thiazol-2′-oxy-5-methylene-N-sec-butyloxazolidine;
thiazol-2′-oxy-5-methylene-N-cyclopropyloxazolidine;
thiazol-2′-oxy-5-methylene-N-cyclopentyloxazolidine;
(+)-thiazol-2′-oxy-5-methylene-N-α-phenylethyloxazolidine;
thiazol-2′-oxy-5-methylene-N-γ-phenylpropyloxazolidine;
thiazol-2′-oxy-5-methylene-N-β-(p-hydroxyphenyl)-ethyloxazolidine;
thiazol-2′-oxy-5-methylene-N-[α-methyl-β-(p-hydroxyphenyl)-ethyl]-oxazolidine;
thiazol-2′-oxy-5-methylene-N-γ-(p-hydroxyphenyl)-propyloxazolidine; and
thiazol-2′-oxy-5-methylene-N-[α-methyl-γ-(p-hydroxyphenyl)propyl]-oxazolidine.

The preferred pharmaceutical acceptable salts are hydrogen addition salts of chloride, bromide, sulfate, maleate, lactate, tartrate, succinate and especially chloride and maleate. Thus the preferred salts are the preferred anion addition salts of formulas I and III and corresponding the particularly preferred salts are the preferred hydrogen anion addition salts of the preferred and particularly preferred compounds of formulas I and III and especially the hydrochloride and maleate addition salts.

One process, according to the invention, for preparing the compounds of formulas I and II, of the invention, can be conveniently represented by the following schematic overall reaction equations:

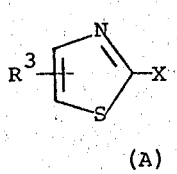

(A)

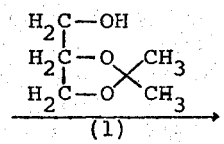

(1)

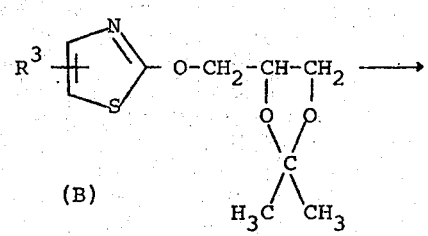

(B)

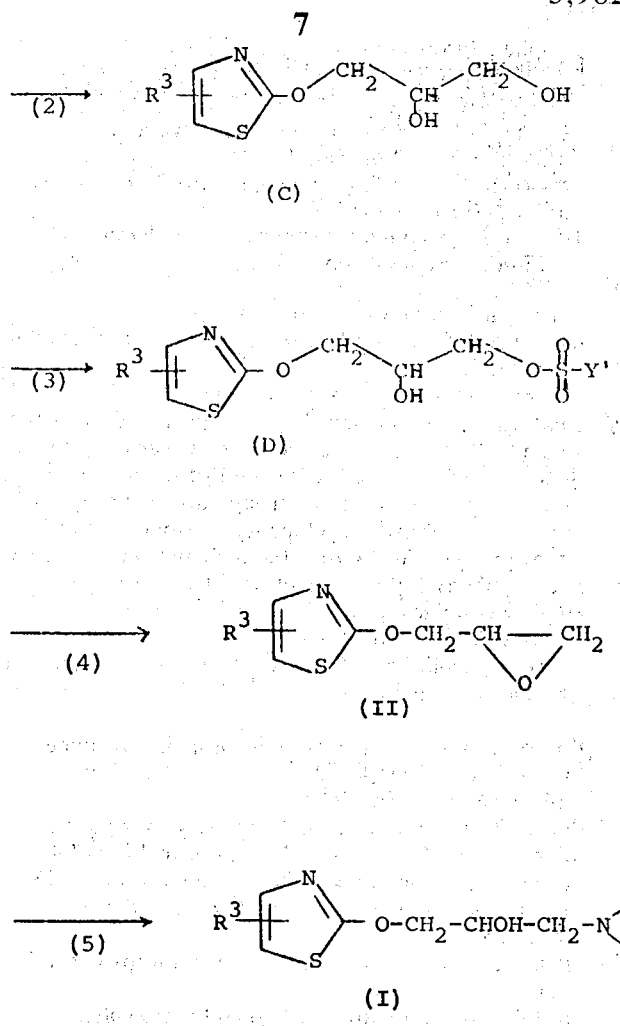

wherein X is bromo or chloro, Y' is alkyl or phenyl, and R¹, R², and R³ have the same meanings as set forth herein above.

Step 1 of the above process can be effected by treating the thiazole compound of formula A with glycerol acetonide in a suitable inert solvent, in the presence of an alkali metal hydride. Typically, this treatment is conducted at temperatures in the range of about from 20°C to reflux for about from a few minutes to 20 hours, using mole ratios in the range of about from 1 to 100 moles of glycerol acetonide per mole of compound A. However, temperature, reaction times, and mole ratios both above and below can also be used. Suitable alkali metal hydrides which can be used include, for example, sodium hydride, potassium hydride, calcium hydride, lithium hydride and the like. Suitable inert organic solvents which can be used include, for example, monoglyme, tetrahydrofuran, diglyme, dimethylformamide, and the like. Also an excess of glycerol acetonide can be used as the solvent. Further by using the optically pure (+) glycerol acetonide isomer (see *J. Biol. Chem.* v. 128, p. 463 (1939)) or the optically pure (−) glycerol acetonide isomer (see *J. Am. Chem. Soc.* v. 67, p. 944 (1945)) the corresponding (+) or (−) optically active isomer of formula B is obtained. Correspondingly, wherein a (+) and (−) isomer mixture of the glycerol acetonide is used, the product will similarly be a mixture of isomers. This optically active isomer relationship between the starting materials and products exist throughout all the steps of various processes described herein. Also typically and conveniently, a racemic glycerol acetonide isomer mixture will be used and thus typically the product will correspondingly be a racemic mixture.

Step 2, can be conveniently effected by treating the compound of formula B with a suitable organic or inorganic acid, preferably in a suitable inert solvent. Typically this treatment is conducted at temperatures in the range of about from 0° to 65°C and preferably about 25°-30°C, for about from three minutes to 18 hours and preferably about from 1 to 4 hours. However, temperatures, reaction times and mole ratios both above and below these ranges can also be used. Suitable inorganic acids which can be used include, for example, hydrochloric acid, hydrobromic acid, sulfuric acid, phosphoric acid and the like. Suitable organic acids which can be used include, for example, formic acid, oxalic acid, acetic acid, propionic acid, and the like. Suitable solvents which can be used include, for example, water, methanol, acetone, monoglyme, ether and the like. Good results are typically obtained by using aqueous formic acid solution.

Step 3 of the above process can be effected by treating the compound of formula C with a suitable phenyl sulfonyl chloride or bromide or alkyl sulfonyl chloride or bromide, in a suitable organic solvent. The particular sulfonyl derivative used is largely immaterial since the sulfonyl substituent is split off during the next step. Thus, typically other phenyl sulfonyl chloride or bromide or alkyl sulfonyl chloride or bromide derivatives can also be used. Typically this treatment is conducted at temperatures in the range of about from 0° to 60°C and preferably about from 0° to 25°C for about from 5 minutes to 18 hours, preferably about from 10 minutes to 45 minutes, using mole ratios in the range of about from 1.0 to 1.1 moles of sulfonyl derivative per mole of compound of formula C. However, temperatures, treatment times, and mole ratios both above and below these ranges can also be used. Suitable phenyl sulfonyl chlorides or bromides, which can be used include, for example, benzene sulfonyl chloride, benzene sulfonyl bromide, or p-toluene sulfonyl chloride, p-ethyl benzene sulfonyl bromide, and the like. Suitable alkyl sulfonyl chlorides, and bromides, which can be used include, for example, methane sulfonyl chloride, methane sulfonyl bromide and the like. Suitable organic solvents which can be used include, for example, pyridine, triethylamine or other tertiary amines, and the like.

Step 4 can be conveniently effected by treating the compound of formula D with a strong base preferably in an inert organic solvent. Conveniently this treatment is conducted by adding a strong base directly to the product reaction mixture of step 3 without separation of the product of formula D from the reaction mixture. The treatment can, of course, also be applied to the isolated product of formula D. Typically, this treatment is conducted at temperatures in the range of about from 0° to 100°C, preferably about from 20° to 60°C for from ½ hour to 3 hours, and preferably about from ½ hour to 1 hour. However, temperatures and reaction times both above and below these ranges can also be used. Suitable strong bases which can be used include, for example, alkali metal hydroxides such as, for example, sodium hydroxide, potassium hydroxide, and the like, and alkali metal alkoxides such as, for example, sodium methoxide, potassium methoxide, and alkyl or aryl lithiums such as butyl lithium, octyl lithium, phenyl lithium and the like. Suitable inert organic solvents include, for example, monoglyme, ethyl ether, benzene and the like.

Step 5 can be conducted by treating the intermediate product of formula II, of the invention, with the desired $R^1$, $R^2$ amine or amino derivative or N-heterocyclic derivative, including amines incorporated in cyclic systems. For example by treating the compound of formula II with alcoholic solution of ammonia, the corresponding compounds of formula I wherein each of $R^1$ and $R^2$ is hydrogen is obtained. Similarly, treatment with a monoalkyl amine will yield the corresponding compound of formula I wherein one of $R^1$ or $R^2$ is the corresponding alkyl group and the other is hydrogen, and where a dialkyl amine is used, each of $R^1$ and $R^2$ will be alkyl group. Correspondingly, using a nitrogen heterocyclic such as, for example, piperidine; pyrrolidine; or morpholine will afford the corresponding $N_1$-piperidino; $N_1$-pyrrolidinyl; or $N_1$-morpholino, respectively, compounds of formula I. Further although optimum conditions and solvents will vary with the particular intermediate of formula II and ammonia or amino- type derivatives used, the treatment is typically conducted at temperatures in the range of about from 25° to 100°C for about from 10 minutes to 18 hours. However, temperature ranges both above and below these can also be used. Suitable solvents which can be used include, for example, monoglyme, methanol, ethanol, pyridine and the like.

Also although not specifically stated, it should be understood, as would be apparent to one having ordinary skill in the art, that where the starting material for a given step has free hydroxy or free amino groups, which could interfere with the treatment, such groups are preferably protected with conventional labile ester or ether groups by procedures which are well within the scope of the art. For example, with respect to step 3, free hydroxy groups, other than the 1 and 2 hydroxy propane groups, are conveniently protected by treatment with acetic anhydride. The acetate protecting group can then be conveniently removed, after the treatment of step 3, via treatment with a mild base.

Preferably, with the exception of step 4 which, as noted above, is conveniently conducted by addition to the previous product reaction mixture, the respective products of each step are isolated prior to their subsequent use as starting materials for the next succeeding step. Separation and isolation can be effected by any suitable separation or purification procedure such as, for example, evaporation, crystallization, chromatography, thin-layer chromatography, etc. Specific illustrations of typical separation and isolation procedures can be had by reference to the corresponding examples described herein below. However, other equivalent separation or isolation procedures could, of course, also be used. Where an isomer mixture of the product of formula I is obtained, for example where racemic glycerol acetonide mixture has been used in step 1, the respective optically active (+) and (−) isomers can be resolved by conventional procedures. Such as, for example, by reacting the compounds of formula I with an optically active acid which will yield pure optical salts of the compounds of formula I and then isolating the respective (+) and (−) optical salts by repeated crystallization.

The initial starting materials of formula A are generally known compounds or can be prepared according to known procedures and/or according to the preparations described herein below, or by obvious modification of such procedures and preparations. For example, procedures for preparing 2,5-dibromothiazole are described in *Recueil des Travaux Chimiques des Pays Base*, volume 73, page 325 (1964) and the 2,4-dibromothiazole in *Bulletin de la Societe Chimique de France*, page 1735 (1962). 2-Bromo-5-nitrothiazole is described in *Helv. Chim. Acta.*, volume 33, page 306 (1950) and 4-acetamido-2-bromothiazole and 4-amino-2-bromothiazole hydrobromide are described in the *Journal of Organic Chemistry*, volume 28, page 1877 (1963).

The compounds of formula I wherein one of $R^1$ or $R^2$ is hydrogen and the other is hydrogen, lower alkyl, or arylalkyl can also be prepared via an alternate process via the intermediates of formula III. This process can be represented by the following schematic overall reaction equations:

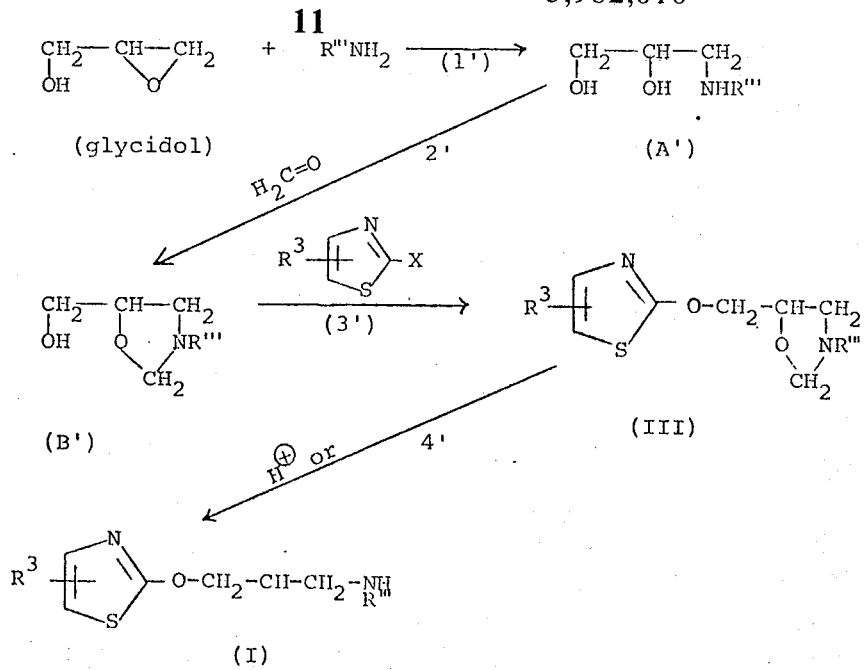

wherein R''' is hydrogen, lower alkyl or arylalkyl and R³ and X are as defined herein above.

Step (1') of the above process can be effected by treating glycidol with ammonia or the desired monosubstituted amine. Typically, this treatment is conducted at temperatures in the range of about from 20°C to reflux and preferably at reflux, for about from 0.5 to 5 hours. Frequently, as the reaction is exothermic and typically will occur at ambient temperature, the reaction can be conducted at reflux without supplying external heat. Also wherein anhydrous ammonia or volatile amines are used, the reaction is typically conducted by passing the gaseous ammonia or substituted amine through a solution of glycidol. Alternatively, suitable inert organic solvents can be used but, typically are unnecessary as glycidol itself is a liquid at room temperature in which the respective substituted amines are usually soluble. Suitable substituted amines which can be used include, for example, methylamine, ethylamine, propylamine, isopropylamine, n-butylamine, t-butylamine, phenylethylamine, p-methylbenzyl, and the like.

Step 2' can be effected by treating the product of step 1', of formula A', with formaldehyde in a suitable inert organic solvent such as, for example, ethanol. Typically, this treatment is conducted at temperatures in the range of about from 20°C below reflux to reflux and preferably at reflux about from 8 to 18 hours. Typically, the formaldehyde is used in the form of an aqueous solution.

Step 3' is preferably conducted in two steps. In the initial phase the 5-hydroxymethyl-3-oxazolidine or 5-hydroxymethyl-substituted oxazolidine product of step 2' (i.e., formula B') is treated with an alkaline metal hydride, e.g., sodium hydride, in a suitable inert organic solvent. Typically, this treatment is conducted at temperatures in the range of about from 20° to 80°C for about from 15 minutes to 5 hours. Preferably this treatment is conducted under anhydrous conditions and preferably conducted in the absence of air, e.g., under an inert gas, e.g., nitrogen. Inert organic solvents which can be used include, for example, dimethylformamide, monoglyme, diglyme, and the like. The second phase of step 3' is conducted by treating the initial product reaction mixture with either 2-chloro or 2-bromothiazole or the desired R³-substituted-2-chloro or 2-bromothiazole. Typically, this treatment is conducted at temperatures in the range of about from 60° to 140°C for about from 1 to 24 hours. Typically, the 2-halo thiazole reagent will be added to the reaction mixture in the form of a solution in a suitable inert organic solvent. Suitable inert organic solvents which can be used include, for example, dimethylformamide, monoglyme, diglyme, and the like. Again preferably the second phase will also be conducted under anhydrous conditions and preferably conducted in an inert gas such as, for example, nitrogen. Step 4' can be conveniently effected by simple acidic or basic hydrolysis of the intermediate of formula III. Thus, acid hydrolysis can be conveniently effected by treating the compound of formula III with a suitable inert organic acid such as, for example, acetic, formic, oxalic acid and the like or suitable acids such as, for example, hydrochloric, sulfuric, and the like. Preferably the hydrolysis is conducted under mildly acidic conditions. Similarly, basic hydrolysis can be conducted by treating the compound of formula III with a suitable base such as, for example, dilute sodium hydroxide, potassium hydroxide and the like. Preferably the hydrolysis can be conducted under mildly alkaline conditions. Alternatively, the hydrolysis can be conducted via exchange with a suitable ion exchange resin in either the H⁺ or OH⁻ form.

Again, as noted previously with respect to the first described process of the invention, it should be understood that in each of the aforedescribed preparation and process steps, that where starting materials having free amino or free hydroxy groups which could interfere with the desired treatment are used, such starting materials are first protected with conventional labile ester or ether groups. And again, unless noted to the contrary, it is preferred that the respective products of each process step or preparation step, described herein above, be separated and/or isolated prior to its use as starting material for subsequent steps. Separation and isolation can be effected by any suitable or purification procedure such as, for example, evaporation, crystallization, column chromatography, thin-layer chromatography, distillation etc. Specific illustrations of typical separation and isolation procedures can be had by reference to the appropriate examples described herein below. However, other equivalent separation procedures could, of course, also be used. Also where an isomer mixture of the product of formula I or III is obtained, for example, wherein an isomeric mixture of glycerol acetonide or glycerol has been used in steps 1 and 1', respectively, the respective optically active (+) and (−) isomers can be resolved by known procedures. Optimum resolution procedures can be obtained by routine trial and error procedures well within the scope of those skilled in the art.

The pharmaceutically acceptable acid addition salts of the compounds of formulas I and III can be prepared via neutralization of the parent compound, typically via neutralization of an amino moiety, with the desired acid-anion. Other pharmaceutically acceptable addition salts can then be conveniently prepared from the neutralization addition salts via anion exchange with a suitable ion exchange resin in the desired anion form.

The compounds of formulas I and III, of the invention, are useful in the treatment and palliation of cardiovascular abnormalities in mammals. The compounds of the invention primarily achieve their therapeutic action by affecting the $\beta$-adrenergic receptor sites in mammals. The compounds which primarily function as strong $\beta$-adrenergic stimulating agents (such as, for example, 1-isopropylamino-3-(thiazol-2-oxy)-2-propanol; 1-amino-3-(thiazol-2-oxy)-2-propanol; 1-sec-butylamino-3-(thiazol-2-oxy)-2-propanol; 1-cyclopropylamino-3-(thiazol-2-oxy)-2-propanol; 1-cyclopentylamino-3-(thiazol-2-oxy)-2-propanol; (+)-1-$\alpha$-phenylethylamino-3-(thiazol-2-oxy)-2-propanol; 1-$\gamma$-phenylpropylamino-3-(thiazol-2-oxy)-2-propanol; 1-[$\alpha$-methyl-$\beta$-phenyl]-ethylamino-3-thiazol-2-oxy)-2-propanol; 1-[$\beta$-(3,4-dimethoxyphenyl)]-ethylamino-3-(thiazol-2-oxy)-2-propanol and the corresponding hydrolyzation precursors of formula III are especially useful in the treatment and palliation of acute heart failure (such as, for example, acute heart failure following myocardial infarction), myocardial depression following cardiac surgery, chronic heart failure of all etiologies, bradyarrhythmias, general cardiomyopathic conditions and instances of complete heart block, occurring in mammals. The $\beta$-adrenergic stimulating agents also, as would be expected, typically exhibit a degree of subsequent $\beta$-adrenergic blocking activity. Also generally the compounds of formulas I and III where $R^3$ is hydrogen primarily function as $\beta$-adrenergic stimulating agents and are typically enhanced, with respect to such activity, by the presence of a secondary amine side chain (i.e. one of $R^1$ or $R^2$ is hydrogen) and further enhanced by the presence of a methine hydrogen atom on the $R^1$ or $R^2$ carbon atom which is attached to the amine nitrogen

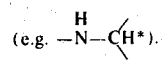

The compounds of formulas I and III can be administered in a wide variety of dosage forms, either alone or in combination with other pharmaceutically compatible medicaments, in the form of pharmaceutical compositions suited for oral or parenteral administration. The compounds are typically administered as pharmaceutical compositions consisting essentially of the pharmaceutically acceptable salts of the compounds of formula I and/or III and a pharmaceutical carrier. The pharmaceutical carrier can be either a solid material or liquid, in which the compound is dissolved, dispersed or suspended, and can optionally contain small amounts of preservatives and/or pH-buffering agents. Suitable preservatives which can be used include, for example, benzyl alcohol and the like. Suitable buffering agents include, for example, sodium acetate and pharmaceutical phosphate salts and the like.

The liquid compositions can, for example, be in the form of solutions, emulsions, suspensions, syrups or elixirs. A preferred mode of administration and composition is intravenous administration of a simple solution of the pharmaceutically acceptable addition salts of the compounds of formula I and/or III in sterile water optionally containing small quantities of preservatives and/or buffering agents.

The solid compositions can take the form of tablets, powders, capsules, pills or the like, preferably in unit dosage forms for simple administration or precise dosages. Suitable solid carriers include, for example, pharmaceutical grades of starch, lactose, sodium saccharin, sodium bisulfite and the like.

The compounds of this invention are typically administered in dosages of about from 0.01 to 5 mg. per kg. of body weight. The precise effective dosage will, of course, vary depending upon the mode of administration, the condition being treated and the host.

A further understanding of the invention can be had from the following non-limiting Examples. Also as used herein above and below unless expressly stated to the contrary, all temperatures and temperature ranges refer to the Centigrade system and the terms ambient or room temperature refer to about 20°C. The term percent or (%) refers to weight percent. The term molar equivalent (m. equiv.) refers to a quantity of reagent equal in moles to the moles of the immediately preceding reactant recited in the examples. Also unless expressly stated to the contrary, racemic mixtures are used as starting materials and correspondingly racemic mixtures are obtained as products and where necessary, preparations and examples are repeated to provide sufficient quantities of starting materials for subsequent examples.

EXAMPLE 1

This example illustrates the first step of the generic process of the invention. In this example sodium hydride (18 g., 56 wt.% dispersion in oil) is washed with n-hexane, and the hexane is replaced with monoglyme (100 ml.). To this mixture is added a solution of glycerol acetonide (44.5 g.) in monoglyme (200 ml.) under an atmosphere of nitrogen. After 15 minutes, 2-chlorothiazole (32 g.) is added, and the mixture is refluxed for 1.25 hours. The reaction mixture is then cooled, diluted with ether and filtered. The filtrate is washed with saturated aqueous sodium chloride solution twice, dried and concentrated by evaporation. Fractional distillation yields 3-(thiazol-2-oxy)-propanediol 1,2-acetonide.

Repeating the above procedure with 2-bromothiazole yields 3-(thiazol-2-oxy)-propanediol 1,2-acetonide.

EXAMPLE 2

This example illustrates methods according to step 2 of the generic process of the invention. In this example one gram of 3-(thiazol-2-oxy)-propanediol 1,2-acetonide in 2 ml. of a 88% aqueous formic acid is stirred at room temperature for 5 minutes. The solution is then evaporated under vacuum at room temperature to yield a residue of 3-(2-thiazoloxy)-1,2-propanediol.

EXAMPLE 3

This example illustrates steps 3 and 4 of the generic process, of the invention, and further illustrates the preparation of the compounds of formula II of the invention. In this example 50 grams of 3-(thiazol-2-oxy)-1,2-propanediol is dissolved in 200 ml. of pyridine at 20°C and then 22.5 ml. of methylsulfonyl chloride is added. The mixture is allowed to stand for 10 minutes and then separated into two portions (1/10 portion and one 9/10 portion). The 1/10 portion is diluted with water, then filtered and the resulting filter cake dried affording 2-hydroxy-1-methylsulfonyloxy-3-(thiazol-2-oxy)-propane.

The remaining 9/10 portion is diluted with one liter of ethyl ether and 200 g. of solid sodium methoxide added in portions during 5–10 minutes. The resulting mixture is stirred at 20°–25°C for one hour, or until complete transformation is demonstrated by thin-layer chromatography, and then poured into water. The ether layer is washed several times with water and then concentrated. The concentrate is diluted with benzene and washed with 20 vol. % aqueous acetic acid three times, then with saturated aqueous sodium chloride solution three times, and then once with an aqueous saturated sodium bicarbonate solution. The organic layer is dried over sodium sulfate and evaporated to remove all residual solvent. The residue is distilled at reduced pressure to yield 1,2-epoxy-3-(thiazol-2-oxy)-propane.

EXAMPLE 4

This example illustrates methods according to the invention of converting the compounds of formula II, of the invention, into the compounds of formula I of the invention. In this example, 300 mg. of 1,2-epoxy-3-(thiazol-2-oxy)-propane is dissolved in 5 ml. of ethanol saturated with ammonia and left at room temperature for 20 hours. The reaction mixture is then evaporated to remove all residual solvent, and the residue is purified by thin-layer chromatography on preparative silica plate using a developing system of 1 percent triethylamine, 1.5 percent methanol and the remainder ethyl acetate to yield 1-amino-3-(thiazol-2-oxy)-propanol.

Similarily by following the same procedure but replacing ammonia with methylamine, dimethylamine and ethylamine, respectively, the corresponding 1-methylamino; 1-dimethylamino; and 1-ethylamino derivatives of the above compound are respectively prepared.

EXAMPLE 5

This example illustrates further methods according to the invention of preparing the compounds of formula I of the invention. In this example 0.6 g. of isopropyl amine is added to a solution of 0.3 g. of 1,2-epoxy-3-(thiazol-2-oxy)-propane in 20 ml. of anhydrous absolute ethanol at 20°C. The resulting mixture is monitored by thin-layer chromatographic analysis and allowed to stand until conversion of 1,2-epoxy-3-(thiazol-2-oxy)-propane is essentially complete. The mixture is then evaporated to dryness yielding a crude residue of 1-isopropylamino-3-(thiazol-2-oxy)-2-propanol which is then further purified by thin-layer chromatography.

1-isopropylamino-3-(4-[N-methylsulfamoyl]-thiazol-2-oxy)-2-propanol;
1-isopropylamino-3-(5-[N,N-dimethylsulfamoyl]-thiazol-2-oxy)-2-propanol;
1-isopropylamino-3-(4-[N,N-dimethylsulfamoyl]-thiazol-2-oxy)-2-propanol;
1-isopropylamino-3-(5-[N-isopropylsulfamoyl]-thiazol-2-oxy)-2-propanol; and
1-isopropylamino-3-(4-[N-isopropylsulfamoyl]-thiazol-2-oxy)-2-propanol.

The hydrochloride addition salt of the above compound is prepared by treating 1 g. of the above compound with 1-equivalent of hydrogen chloride in 50 ml. of ethyl ether saturated with dry hydrogen chloride: gas at 20°C for 1 hour.

Similarily by following the same procedure as above but using t-butylamine in place of isopropylamine, the corresponding 1-t-butylamine derivative of the above compound and its hydrogen chloride addition salt is prepared.

EXAMPLE 6

This example illustrates further methods according to the invention of preparing the compounds of formula I of the invention. In this example 1 g. of morpholine is added to a solution of 0.3 g. of 1,2-epoxy-3-(thiazol-2-oxy)-propane in 20 ml. of anhydrous absolute ethanol at 20°C. The resulting mixture is monitored by thin-layer chromatographic analysis and allowed to stand until conversion of 1,2-epoxy-3-(thiazol-2-oxy)-propane is essentially complete. The mixture is then evaporated to dryness yielding a crude residue of 1-(N-morpholino-3-(thiazol-2-oxy)-2-propanol which is then further purified by thin-layer chromatography.

The hydrochloride addition salt of the above product is prepared by treating the above product with hydrogen chloride as described in Example 5.

Similarly by following the same procedure but respectively using pyrrolidine and piperidine in place of morpholine, the 1-(N-pyrrolidinyl) and 1-(N-piperidinyl) derivatives of the above 1-(N-morpholino) product and their hydrochloride addition salts are respectively prepared.

EXAMPLE 7

This example illustrates further methods according to the invention of preparing the compounds of formula I of the invention. In this example 0.6 g. of ethanolamine is added to a solution of 0.3 g. of 1,2-epoxy-3-(thiazol-2-oxy)-propane in 20 ml. of anhydrous absolute ethanol at 20°C. The resulting mixture is monitored by thin-layer chromatographic analysis and allowed to stand until conversion of 1,2-epoxy-3-(thiazol-2-oxy)-propane is essentially complete. The mixture is then evaporated to dryness yielding a crude residue of 1-($\beta$-hydroxyethylamino)-3-(thiazol-2-oxy)-2-propanol which is then further purified by thin-layer chromatography.

The corresponding hydrogen addition salt of the above product is prepared by treating the 1-($\beta$-hydroxyethylamino) product with hydrogen chloride as described in Example 5.

Similarly by following the same procedure but respectively using 1-amino-1-phenylethane; β-(p-hydroxyphenyl)-ethylamine; α-methyl-β-(p-hydroxyphenyl)-ethylamine; γ-(p-hydroxyphenyl)-propylamine; and α-methyl-γ-(p-hydroxyphenyl)-propylamine in place of ethanolamine, the corresponding 1-(N-[α-phenylethyl]amino); 1-(β-[p-hydroxyphenyl]-ethylamino); 1-(α-methyl-β-[p-hydroxyphenyl]-ethylamino); 1-γ-[p-hydroxyphenyl]-propylamino); and 1(α-methyl-γ-[p-hydroxyphenyl]-propylamino) derivatives of the above product and their hydrochloride addition salts are respectively prepared.

EXAMPLE 8

This example illustrates methods according to the invention of preparing the compounds of formula I of the invention. In this example the procedure of Example 5 is followed but respectively treating 1,2-epoxy-3-(thiazol-2-oxy)-propane with each of the compounds listed in Column J, yielding the corresponding compounds listed in Column K. Also where pure optical isomer products are indicated in Column K, the corresponding optical isomer of 1,2-epoxy-3-(5-thiazol-2-oxy)-2-propane is used as starting material.

COLUMN J ethylamine;
isopropylamine;
isopropylamine;
isopropylamine;
α-methylpropylamine (i.e. sec-butylamine);
t-butylamine;
cyclopropylamine;
cyclopentylamine;
allylamine;
ethanolamine;
diethanolamine;
α-methyl-β-hydroxyethylamine;
β-methoxyethylamine;
γ-dimethylaminopropylamine;
benzylamine;
benzylamine;
benzylamine;
α-phenylethylamine;
α-phenylethylamine;
α-phenylethylamine;
α-methyl-β-phenylethylamine;
α-methyl-β-phenylethylamine;
α-methyl-β-phenylethylamine;
γ-phenylpropylamine;
α-methyl-β-(p-methoxyphenyl)-ethylamine;
β-(3,4-dimethoxyphenyl)-ethylamine;
morpholine;
γ-(N-piperidino)-propylamine; and
N-(N-β-hydroxyethyl)-piperazine.

COLUMN K 1-ethylamino-3-(thiazol-2-oxy)-2-propanol;
1-isopropylamino-3-(thiazol-2-oxy)-2-propanol;
(+)-1-isopropylamino-3-(thiazol-2-oxy)-2-propanol;
(−)-1-isopropylamino-3-(thiazol-2-oxy)-2-propanol;
1-α-methylpropylamino-3-(thiazol-2-oxy)-2-propanol;
1-t-butylamino-3-(thiazol-2-oxy)-2-propanol;
1-cyclopropylamino-3-(thiazol-2-oxy)-2-propanol;
1-cyclopentylamino-3-(thiazol-2-oxy)-2-propanol;
1-allylamino-3-(thiazol-2-oxy)-2-propanol;
1-β-hydroxyethylamino-3-(thiazol-2-oxy)-2-propanol;
1-di(β-hydroxyethyl)amino-3-(thiazol-2-oxy)-2-propanol;
1(α-methyl-β-hydroxyethylamino)-3-(thiazol-2-oxy)-2-propanol;
1-β-methoxyethylamino-3-(thiazol-2-oxy)-2-propanol;
1-γ-dimethylaminopropylamino-3-(thiazol-2-oxy)-2-propanol;
1-benzylamino-3-(thiazol-2-oxy)-2-propanol;
(+)-1-benzylamino-3-(thiazol-2-oxy)-2-propanol;
(−)-1-benzylamino-3-(thiazol-2-oxy)-2-propanol;
1-α-phenylethylamino-3-(thiazol-2-oxy)-2-propanol;
(+)-1-α-phenylethylamino-3-(thiazol-2-oxy)-2-propanol;
(−)-1-α-phenylethylamino-3-(thiazol-2-oxy)-2-propanol;
1-(α-methyl-β-phenylethylamino)-3-(thiazol-2-oxy)-2-propanol;
(+)-1-(α-methyl-β-phenylethylamino)-3-(thiazol-2-oxy)-2-propanol;
(−)-1-(α-methyl-β-phenylethylamino)-3-(thiazol-2-oxy)-2-propanol;
1-γ-phenylpropylamino-3-(thiazol-2-oxy)-2-propanol;
1-[α-methyl-β-(p-methoxyphenyl)-ethylamino]-3-(thiazol-2-oxy)-2-propanol;
1-[β(3,4-dimethoxyphenyl)-ethylamino]-3-(thiazol-2-oxy)-2-propanol;
1-(N-morpholino)-3-(thiazol-2-oxy)-2-propanol;
1-[γ-(N-piperidino)-propylamino]-3-(thiazol-2-oxy)-2-propanol; and
1-[N-(4-hydroxyethyl)-piperazinyl]-3-(thiazol-2-oxy)-2-propanol.

By following the salt preparation procedures of Examples 13 and 14, using the corresponding compounds of Column K as starting materials, the following salts are respectively prepared:

1 ethylamino-3-(thiazol-2-oxy)-2-propanol hydrochloride;
1-isopropylamino-3-(thiazol-2-oxy)-2-propanol hydrochloride;
(+)-1-isopropylamino-3-(thiazol-2-oxy)-2-propanol hydrochloride;
(−)-1-isopropylamino-3-(thiazol-2-oxy)-2-propanol hydrochloride;
1-α-methylpropylamino-3-(thiazol-2-oxy)-2-propanol maleate salt;
1-t-butylamino-3-(thiazol-2-oxy)-2-propanol maleate salt;
1-cyclopropylamino-3-(thiazol-2-oxy)-2-propanol maleate salt;
1-cyclopentylamino-3-(thiazol-2-oxy)-2-propanol maleate salt;
1-allylamino-3-(thiazol-2-oxy)-2-propanol maleate salt;
1-β-hydroxyethylamino-3-(thiazol-2-oxy)-2-propanol hydrochloride;
1(α-methyl-β-hydroxyethylamino)-3-(thiazol-2-oxy)-2-propanol maleate salt;
1-β-methoxyethylamino-3-(thiazol-2-oxy)-2-propanol maleate salt;
1-γ-dimethylaminopropylamino-3-(thiazol-2-oxy)-2-propanol bis-maleate salt;
1-benzylamino-3-(thiazol-2-oxy)-2-propanol bis-maleate salt;
(+)-1-benzylamino-3-(thiazol-2-oxy)-2-propanol bis-maleate salt;

(−)-1-benzylamino-3-(thiazol-2-oxy)-2-propanol bis-maleate salt;
1-α-phenylethylamino-3-(thiazol-2-oxy)-2-propanol maleate salt;
(+)-1-α-phenylethylamino-3-(thiazol-2-oxy)-2-propanol maleate salt;
(−)-1-α-phenylethylamino-3-(thiazol-2-oxy)-2-propanol maleate salt;
1-(α-methyl-β-phenylethylamino)-3-(thiazol-2-oxy)-2-propanol maleate salt;
(+)-1-(α-methyl-β-phenylethylamino)-3-(thiazol-2-oxy)-2-propanol maleate salt;
(−)-1-(α-methyl-β-phenylethylamino)-3-(thiazol-2-oxy)-2-propanol maleate salt;
1-[α-methyl-β-(p-methoxyphenyl)-ethylamino]-3-(thiazol-2-oxy)-2-propanol maleate salt;
1-[N-(4-hydroxyethyl)-piperazinyl]-3-(thiazol-2-oxy)-2-propanol bis-maleate salt;
(+)-1-benzylamino-3-(thiazol-2-oxy)-2-propanol maleate salt;
and (−)-1-benzylamino-3-(thiazol-2-oxy)-2-propanol maleate salt.

EXAMPLE 9

This example illustrates steps 1' and 2' of the alternative process of the invention. In this example 25 ml. of racemic glycidol and 50 ml. of t-butylamine are mixed together at room temperature. After about 30 minutes the mixture boils spontaneously and is then allowed to stand at room temperature for an additional 20 hours. The reaction mixture is then concentrated via evaporation to a viscous oil which is then dissolved in a solution containing 250 ml. of ethanol and 50 ml. of 37% (wt.) aqueous formaldehyde. The resulting mixture is refluxed for 18 hours and then evaporated, under vacuum, affording 5-hydroxymethyl-N-t-butyloxazolidine which is then further purified by distillation. Similarly, by following the same procedure but replacing t-butylamine with anhydrous ammonia, methylamine, isopropylamine, benzylamine, and α-methyl-β-phenylethylamine, respectively, the following compounds are respectively prepared:

5-hydroxymethyloxazolidine;
5-hydroxymethyl-N-methyloxazolidine;
5-hydroxymethyl-N-isopropyloxazolidine;
5-hydroxymethyl-N-benzyloxazolidine; and
5-hydroxymethyl-N-(α-[α-methyl-β-phenylethyl])-oxazolidine.

Also in the case of the volatile reagents (i.e., ammonia and methylamine), the procedure is conducted in a closed system by first bubbling the requisite amount of ammonia or methylamine through the glycidol and then sealing the reaction vessel.

EXAMPLE 10

This example illustrates methods, according to the invention, of preparing the compounds of formula III of the invention. In this example, 1.7 g. of 5-hydroxymethyl-N-t-butyloxazolidine in 5 ml. of anhydrous dimethylformamide is added to a suspension of 0.53 g. of sodium hydride in 5 ml. of dimethylformamide, under a nitrogen atmosphere. The resulting mixture is heated at 80°C for 15 minutes and then cooled to room temperature and 1.66 g. of 2-bromothiazole in 10 ml. of anhydrous dimethylformamide added. The mixture is heated at 80°C for 2 hours, then cooled to room temperature and evaporated under high vacuum affording a residue of thiazol-2-oxy-methylene-5'-N-t-butyloxazolidine.

Similarly by following the same procedure the N-methyloxazolidine; N-isopropyloxazolidine; N-benzyloxazolidine and N-(α-[α-methyl-β-phenylethyl])-oxazolidine derivatives of the above product is respectively prepared by using the corresponding 5-hydroxymethyl-N-methyloxazolidine;
5-hydroxymethyl-N-isopropyloxazolidine;
5-hydroxymethyl-N-benzyloxazolidine; and
5-hydroxymethyl-N-(α-[α-methyl-β-phenylethyl]) derivatives as starting materials.

EXAMPLE 11

This example illustrates methods of converting the compounds of formula III into the compounds of formula I of the invention. In this example 1 g. of thiazol-2'-oxy-methylene-N-t-butyloxazolidine is dissolved in 50 ml. of ethyl acetate and this solution is washed three times with aqueous 5% sodium hydroxide (20 ml.) at 20°C. The mixture is allowed to stand for 0.5 hours, washed with water, dried over magnesium sulfate and then evaporated to dryness affording 3-[thiazol-2-oxy]-1-t-butylamino-2-propanol, which is then further purified by chromatography on silica gel plates.

Similarily by following the same procedure, the compounds of formula III, enumerated in Example 10, are respectively hydrolyzed to the corresponding compounds of formula I.

EXAMPLE 12

This example illustrates an alternate method for converting compounds of formula III to compounds of formula I. In this example 1 g. of thiazol-2'-oxy-methylene-N-t-butyloxazolidine is dissolved in 20 ml. of methanol containing 4 cc. of 5% aqueous hydrochloric acid at 20°C. After 15 minutes, the mixture is neutralized with dilute aqueous sodium carbonate solution, poured into water and extracted with ethyl acetate. The ethyl acetate extract is evaporated to dryness yielding 1-t-butylamino-3-(thiazol-2-oxy)-2-propanol.

Similarly by following the same procedure, the compounds of formula III, enumerated in Examples 10 and 13, are respectively hydrolyzed to the corresponding compounds of formula I.

EXAMPLE 13

This example illustrates methods of preparing hydrochloride addition salts of the invention. In this example 1 g. of 1-isopropylamino-3-(thiazol-2-oxy)-2-propanol is dissolved in 10 ml. of ethyl ether at 20°C. A stream of gaseous anhydrous hydrogen chloride is passed over the surface of the solution until the supernatent liquid becomes colorless. The resulting precipitate is collected by filtration, washed with ethyl ether and then crystallized from methanol, containing 1% water and 1% acetone, affording crystalline 1-isopropylamino-3-(thiazol-2-oxy)-2-propanol hydrochloride.

Similarly by following the same procedure using each of the compounds of formula I, enumerated in Examples 4, 5, 6, 7, 8 and 9 and the compounds of formula III enumerated in Example 10 as starting materials, the corresponding hydrochloride addition salts of each of these compounds is respectively prepared.

EXAMPLE 14

This example illustrates methods of preparing the maleate addition salts of compounds of formulas I and III. In this example 1 gram of 1-isopropylamino-3-(thiazol-2-oxy)-2-propanol is dissolved in a solution of 5 ml. of ethyl ether and 5 ml. of ethanol at 20°C. To this solution is added 10 ml. of a saturated solution maleic acid in ethyl ether. The mixture is allowed to stand for 1 hour at room temperature. The resulting precipitate is recovered by filtration, washed three times with ethyl ether and then crystallized from a 1:1, by vol., solution of ethyl ether and ethanol affording crystalline 1-isopropylamino-3-(thiazol-2-oxy)-2-propanol maleate salt.

Similarly by following the same procedure using each of the compounds of formula I, enumerated in Examples 4, 5, 6, 7, 8 and 9 and the compounds of formula III enumerated in Example 10 as starting materials, the corresponding maleate addition salts of each of these compounds is respectively prepared.

EXAMPLE 15

This example illustrates the preparation, according to the invention, of the pure (+) optical isomers of the compounds of formulas I, II and III. In this example, the procedures of Examples 1–14 are repeated but in this instance, in place of racemic glycerol acetonide, the pure (+) optical isomer of glycerol acetonide is used as starting material in Example 1, and in the case of Example 9, the pure (+) optical isomer of glycerol is used in place of racemic glycerol.

EXAMPLE 22

This example illustrates the preparation, according to the invention, of the pure (−) optical isomers of the compounds of formulas I, II and III. In this example, the procedures of Examples 1–20 are repeated but in this instance, in place of racemic glycerol acetonide, the pure (−) optical isomer of glycerol acetonide is used as starting material in Example 1, and in the case of Example 9, the pure (−) optical isomer of glycerol is used in place of racemic glycerol.

Obviously many modifications and variations of the invention described herein above and below in the claims can be made without departing from the essence and scope thereof.

What is claimed is:

1. A pharmaceutical composition, for treating cardiovascular disorders in mammals by stimulating β-adrenergic receptor sites, consisting essentially of a pharmaceutically acceptable carrier and an effective amount of β-adrenergic stimulating agent selected from the group consisting of a pharmaceutically acceptable salt of a compound having the formula

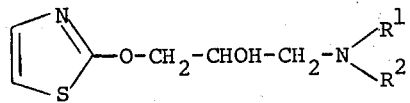

wherein one of $R^1$ or $R^2$ is hydrogen and the other is selected from the group consisting of hydrogen, lower alkyl, cycloalkyl having 3 through 7 ring atoms, lower alkenyl, phenyl, phenylalkyl having up to 12 carbon atoms, alkylphenyl having up to 12 carbon atoms, α-methyl-β-phenylethyl, β-(3,4-dimethoxyphenyl)-ethyl, hydroxy lower alkyl, (lower alkoxy) lower alkyl, and the groups having the formulas —R'X or $$-(CH_2)_n-N\begin{matrix}R^7\\R^8\end{matrix}$$

wherein R' is lower alkyl, X is morpholine, piperidine or pyrrolidine, $R^7$ and $R^8$ are independently hydrogen or lower alkyl and $n$ is a whole integer of from 1 through 4; and mixtures thereof.

2. The composition of claim 1 wherein one of $R^1$ and $R^2$ is a substituent having a methine hydrogen atom on the carbon atom attached to the amino nitrogen atom.

3. The composition of claim 1 wherein one of $R^1$ or $R^2$ is hydrogen and the other is selected from the group consisting of isopropyl; hydrogen; sec-butyl; cyclopropyl; cyclopentyl; α-phenylethyl; γ-phenylpropyl; α-methyl-β-phenylethyl; and β-(3,4-dimethoxyphenyl)-ethyl and wherein when one of $R^1$ or $R^2$ is α-phenylethyl, the compound is the (+) isomer.

4. The composition of claim 1 wherein said carrier is sterile water.

5. The composition of claim 1 wherein said carrier is a solid selected from the group of pharmaceutical grades of starch, lactose, sodium saccharin, sodium bisulfite and mixtures of such carriers.

6. The composition of claim 1 wherein said pharmaceutically acceptable salt is a pharmaceutically acceptable salt of 1-isopropylamino-3-(thiazol-2-oxy)-2-propanol.

7. The composition of claim 6 wherein said pharmaceutically acceptable salt is 1-isopropylamino-3-(thiazol-2-oxy)-2-propanol hydrochloride.

* * * * *